United States Patent
Frering et al.

(10) Patent No.: US 8,657,735 B2
(45) Date of Patent: Feb. 25, 2014

(54) GASTRIC BELT

(75) Inventors: Vincent Frering, Lyons (FR);
Pierre-André Denis, Villeurbanne (FR)

(73) Assignee: Medical Innovation Developpement, Limonest (FR)

( * ) Notice: Subject to any disclaimer, the term of this patent is extended or adjusted under 35 U.S.C. 154(b) by 925 days.

(21) Appl. No.: 10/586,344

(22) PCT Filed: Jan. 14, 2005

(86) PCT No.: PCT/FR2005/000083
§ 371 (c)(1),
(2), (4) Date: Aug. 7, 2008

(87) PCT Pub. No.: WO2005/072664
PCT Pub. Date: Aug. 11, 2005

(65) Prior Publication Data
US 2008/0294180 A1    Nov. 27, 2008

(30) Foreign Application Priority Data
Jan. 16, 2004   (FR) ...................................... 04 00392

(51) Int. Cl.
*A61F 2/00* (2006.01)

(52) U.S. Cl.
USPC ............................................. 600/37

(58) Field of Classification Search
USPC .......................... 600/29–32, 37; 606/151, 157
See application file for complete search history.

(56) References Cited

U.S. PATENT DOCUMENTS

| | | | | |
|---|---|---|---|---|
| 4,634,443 A | * | 1/1987 | Haber | 600/31 |
| 5,152,770 A | | 10/1992 | Bengmark et al. | |
| 2003/0220539 A1 | * | 11/2003 | George et al. | 600/40 |

FOREIGN PATENT DOCUMENTS

| | | |
|---|---|---|
| EP | 0 769 282 A1 | 4/1997 |
| FR | 2 799 118 | 4/2001 |
| WO | WO 00/00108 | 1/2000 |

* cited by examiner

Primary Examiner — Christine Matthews
(74) Attorney, Agent, or Firm — Clark & Brody

(57) ABSTRACT

A gastric belt has a wall of a chamber (3) forming a working face (5) with a length ($l_5$) in the flat position of the belt. The length ($l_5$) is equal to or greater than a length ($l_4$) of the wall of the chamber (3), which forms the back side (4) in such a way that when the belt is fastened in the form of a circle and is inflated, the chamber wall forms folds.

26 Claims, 3 Drawing Sheets

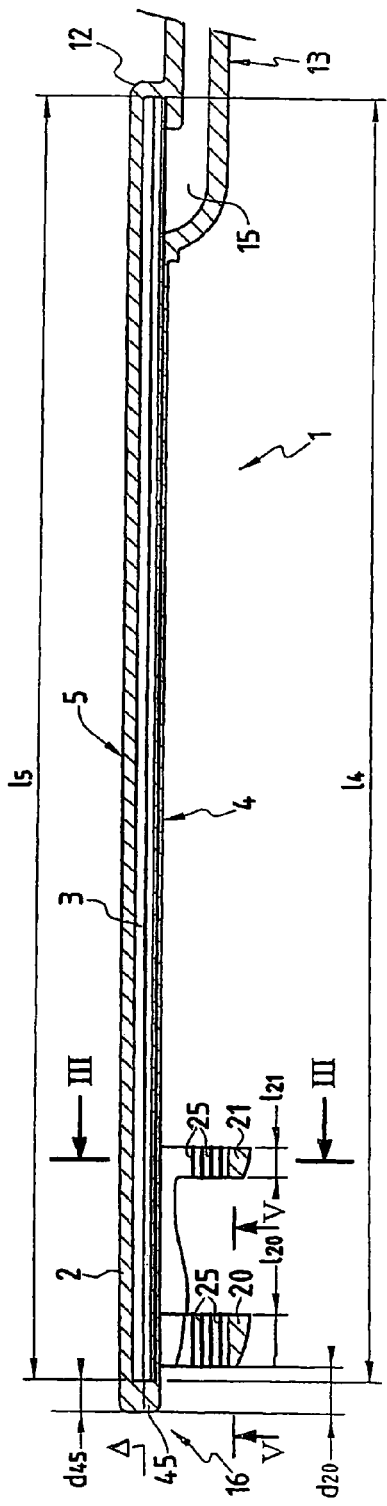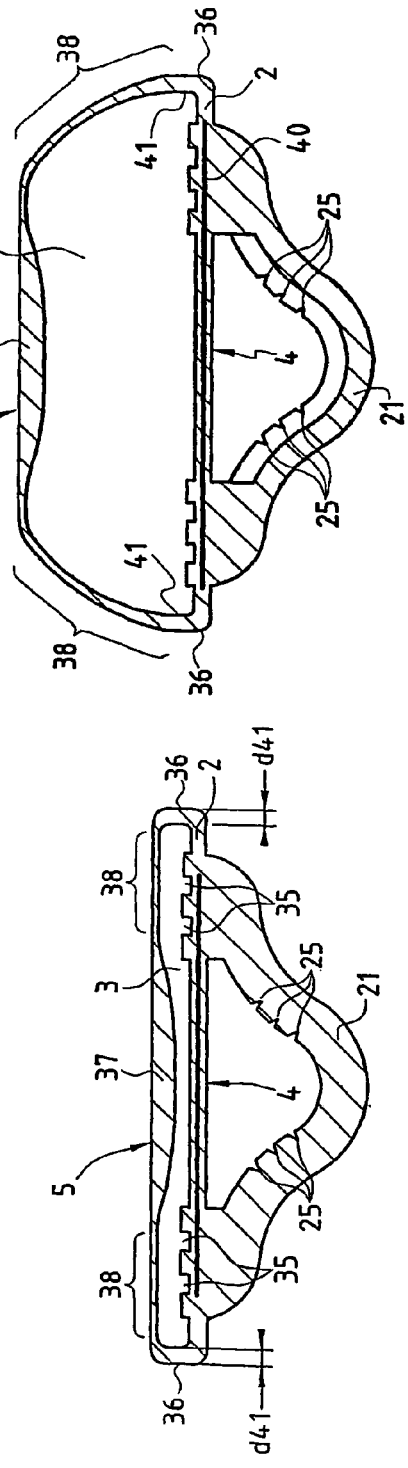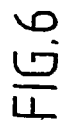

GASTRIC BELT

The invention relates to the technical field of devices for implanting in the connecting zone between the abdominal part of the oesophagus and the stomach, so as to create local restriction allowing control of the quantity of food ingested by the patient wearing the device.

So as to ensure this local restriction, it is known to utilise a belt or inflatable gastric ring, such as for example described in patent applications EP 0 769 282 and FR 2 799 118.

According to these documents, the inflatable gastric belt comprises an elongated flat tubular body, made of supple material, which is, in part at least, elastically deformable and which defines a tight inflatable chamber to present a work face to be placed in contact with the stomach and a back opposite the work face.

To allow the ring belt to close, the latter likewise comprises connecting means equipping the ends of the tubular body and allowing the gastric belt in the form of a ring to close, the work face naturally being oriented inwards. Finally, the gastric belt likewise comprises an inflation catheter connected tightly to the inflatable chamber and intended to be connected to inflation means. The inflation means can be, for example, constituted by a box provided with an auto-closable membrane which can be transpierced by a syringe needle or the like, by means of which an injection can be given or fluid can be taken, such as, for example though not necessarily, physiological serum, to control the inflation of the chamber and thus the dimensions of the cinching on the stomach made by means of the inflatable gastric belt.

According to these documents, the tubular body and the inflatable chamber are embodies so as to form, after closing of the belt and inflation of the latter, a ring of regular cross-section.

Now, if such belts have generally given satisfaction and, after their implantation in the majority of cases, have achieved the desired therapeutic effect, in a lesser number of cases displacement phenomena of the inflatable belt around the oesophagus or the upper part of the stomach has been observed, causing inflammation of the tissues in contact with the inflatable gastric belt, justifying re-intervention and removal of said belt.

The need has thus arisen to provide a novel type of inflatable gastric belt which has greater stability for implantation around the stomach or the oesophagus, without the need for suturing the inflatable belt on the wall of the stomach or oesophagus.

To attain this objective the invention relates to an inflatable gastric belt comprising an elongated tubular body made of supple material which is, in part at least, elastically deformable, which defines a tight inflatable chamber and which has a back and a work face;

connecting means arranged in relation to the two ends of the tubular body and allowing the gastric belt to be closed into the shape of a ring, the work face being arranged inside the ring, an inflation catheter connected tightly to the inflatable chamber and intended to be connected to inflation means.

According to the invention, this inflatable gastric belt is characterised in that in the deflated state of the belt the wall of the chamber forming the work face has a length greater than or equal to that of the wall of the chamber forming the back, such that, during closing of the ring belt and after inflation, the wall of the chamber constituting the work face forms folds.

This characteristic of the invention thus enables the formation of folds during inflation of the belt, such that the interior of said belt does not have the regular shape of a ring but, on the contrary, a star shape or irregular hypocycloid. These folds form randomly and not in a predetermined fashion, as a function of the form, movements and resistance to compression of the wall of the stomach. Accordingly, the folds are susceptible to be moved during utilisation of the belt, such that the compression points on the stomach wall likewise move, avoiding necroses or local inflammations.

In fact, the inventors thought to reveal the fact that such an irregular form during inflation ensured better stability of the inflatable gastric belt and, contrary to another idea, the pinching zones it is eventually likely to create on the outer wall of the oesophagus or stomach do not increase erosion or inflammation phenomena of the latter. This advantageous characteristic of the invention claims that the inflation fluid circulates from one compartment, defined by the folds, to the other, ensuring equilibrium of the inflation pressure and thus better distribution of forces applied to the stomach.

Still in the same sense and according to a preferred though not strictly necessary form of the invention, the inflatable gastric belt is embodied such that its tubular body has, in the deflated state of the chamber and when the belt is not closed, a substantially flat form, without pre-configuration. In this state, which could be qualified as a rest state, the inflatable gastric belt has a substantially rectangular parallelepipedic form, an abstraction made of the connecting means, the walls of the inflatable chamber, in relation to the work face and the back, being substantially flat and parallel. This characteristic of the invention on the one hand allows random positioning of the folds during inflation of the belt and, on the other hand, displacement of these same folds during application of constraints to the belt by the stomach.

According to a characteristic of the invention, in order to prevent possible problems of inflation at the folds formed by the work face of the belt, the internal face of the wall of the chamber comprises at least one groove of longitudinal direction for defining an internal duct for circulation of the inflation fluid at the level of the fold or folds formed. According to the invention, the longitudinal groove does not necessarily extend over the entire length of the inflatable chamber, but over a part at least of this length and, for example though not exclusively, in a median region of the chamber and over a length greater than or equal to half of the length of the inflatable chamber.

According to a preferred though not strictly necessary form, the internal face of the wall of the inflatable chamber comprises at least one row of parallel longitudinal grooves.

According to the invention, this groove or this row of grooves can be made at any point of the wall of the inflatable chamber. All the same, the longitudinal grooves will preferably be arranged on the internal face of the inflatable chamber corresponding to the back of the belt.

Preferably though not strictly necessary, the internal face of the inflatable chamber, corresponding to the back of the belt, comprises two rows of parallel longitudinal grooves, each row being situated near an edge of the back of the belt.

According to another characteristic of the invention and still with a view to further augment the stability of the belt during its inflation, the wall of the chamber forming the work face comprises local limitation means of the elasticity of the wall.

In a preferred though not strictly necessary embodiment, the local limitation means of the elasticity occupy a longitudinal median region of the work face, such that, during inflation of the belt, the longitudinal edges of the work face dilate more than the median region of said work face. Therefore, the local limitation means of the elasticity are adapted so that the radius of curvature of the median region of the work face during inflation of the belt is, as far as possible, greater than the radius of curvature of the lateral regions.

According to the invention, the local limitation means of the elasticity of the wall of the inflatable chamber can be made in any appropriate manner, such as, for example, in the form of connected elements, preferably though not necessarily, elastically deformable and fixed to or inserted into the wall of the inflatable chamber.

According to a preferred embodiment, the local limitation means of the elasticity comprise local excessive thickness of the wall of the chamber making up the work face of the belt.

According to yet another characteristic of the invention, each longitudinal edge of the inflation chamber is, preferably though not necessarily, situated at a distance from the corresponding longitudinal edge of the body of the gastric belt.

This characteristic of the invention likewise contributes to greater stability of the gastric belt during its implantation and after inflation of the latter. Preferably, though not strictly necessary, each longitudinal edge of the inflatable chamber is situated at a distance from the corresponding longitudinal edge of the body of the belt, between 0.50 mm and 2.50 mm and, preferably, between 0.65 mm and 0.90 mm.

According to another characteristic of the invention, the wall of the inflatable chamber, forming the back of the belt, comprises at least one inextensible longitudinal supple fitting, such that, when the belt is closed into a ring and during inflation of the chamber, it favours centripetal deformation of the inflatable chamber.

Preferably, though not strictly necessary, the inextensible fitting is thus completely enclosed by the material making up the body of the belt.

Accordingly, the belt is moulded in a single injection procedure to form a single piece around the inextensible fitting, without connected elements other than plugs at the injection points and, optionally, elements making up the connecting means for closing into a ring of the belt.

Furthermore, according to the invention, the connecting means, allowing the closing of the belt in the form of a ring around the oesophagus or the upper part of the stomach, can be made in any appropriate manner. All the same, preferably though not strictly necessary, the connecting means comprise:

in relation to a first so-called inflation end of the body, a connecting tail from the catheter to the inflatable chamber, and, in relation to the opposite so-called free end of the body, at least one bow for receiving the connecting tail.

According to a characteristic of the invention, the connecting tail comprises at least anti-return locking means for cooperating with the bow.

According to the invention, the anti-return locking means can be made in any appropriate manner. According to a preferred though not strictly necessary embodiment, the locking means comprise at least configuration as a spruce tree or lanceolated.

According to another characteristic of the invention, the bow is arranged at the back of the belt, so as to avoid the risk of injury to the wall of the oesophagus or stomach.

According to a characteristic of the invention, the connecting means comprise at least two aligned bows. Preferably, the bow, situated closest to the free end of the body, has a shape flared towards the free end of the belt and converging towards the second ring, so as to ensure guidance of the catheter towards the second bow during the procedure of closing the belt.

The width of the bow is preferably greater than 6 mm to ensure optimal guidance.

According to a characteristic of the invention, in order to prevent deviation of the two ends of the body when the belt is closed, the ring closest to the free end is situated at a distance from the free end less than 5 mm and, preferably, less than 3 mm, this distance being measured between a transversal plane passing via the apex of the bow at its part closest to the free end and a parallel plane passing via this free end.

According to yet another characteristic of the invention, the internal face of the bow has specks or stria parallel to the longitudinal axis of the body and in the direction of introduction of the catheter and of the locking tail, so as to reduce friction during passage of the catheter and the tail.

According to another characteristic and still in view of facilitating passage of the catheter, the latter is, preferably though not necessarily, covered in a product having low friction coefficient, such as, for example, Teflon.

According to another characteristic of the invention, one at least of the ends of the inflatable chamber is situated at a distance from the corresponding end of the body to define a reinforced prehension end.

Using such a reinforced end defines a zone particularly appropriate for extracting the gastric belt by forceps, without the risk of perforating the wall of the inflatable chamber.

In one embodiment, the end of the inflatable chamber is thus situated at a distance from the corresponding end of the body greater than 5 mm and, preferably, greater than 7 mm and, more particularly preferred, at a distance of between 7 mm and 15 mm, 10 mm being an advantageous compromise. This provides a full prehension end.

In another embodiment, the end is reinforced by adopting, in the end zone, between the three sides of the inflatable chamber and the corresponding edges of the body of the belt, a distance greater than that adopted for the rest of the belt. Preferably, though not exclusively, this distance, in the end zone, shall be greater than 0.75 mm and, more particularly preferred between 0.75 mm and 2.50 mm, a distance comprise between 1.50 mm and 2.50 mm offering a good compromise.

In the same sense, according to another characteristic of the invention, the wall of the inflatable chamber is reinforced in the vicinity of the free end of the body of the belt and has, to this effect, excessive local thickness in this region.

According to yet another characteristic of the invention, the belt comprises optical position-finding means for the back and/or of the work face of the body. According to a preferred embodiment, the position-finding means comprise optical signs placed on the back of the belt, as well as on the corresponding face of the catheter.

According to another characteristic of the invention, the belt comprises optical indication means of the direction of the free end of the catheter and/or the free end of the body of the belt. According to an embodiment, these optical indication means comprise arrows or triangles whereof one point is oriented towards the free end of the catheter.

Such position-finding means and/or optical indication means thus make the work of the surgeon easier in terms of implantation via celioscope.

According to yet another characteristic of the invention, the free end of the catheter, situated opposite the body of the belt, is blocked by means of a plug of truncated shape which, on the one hand, prevents the introduction of organic material into the catheter when the belt is being positioned and, on the other hand, facilitates introduction of the catheter into the bow or the bows constituting the connecting means.

It is understood that the different characteristics of the invention, mentioned hereinabove, can be utilised together or, in part only, according to different combinations to embody an inflatable gastric belt according to the present invention.

Furthermore, various other characteristics of the invention will emerge from the following description given in reference to the attached diagrams which illustrate a preferred, though not limitative, embodiment of an inflatable gastric belt according to the invention.

FIG. 2 is a longitudinal section according to the plane 11-11 of FIG. 1.

FIG. 3 is a transverse section according to the line III-III of FIG. 2.

FIG. 6 is a section, similar to FIG. 3, in an inflated state of the belt.

Figure 1:
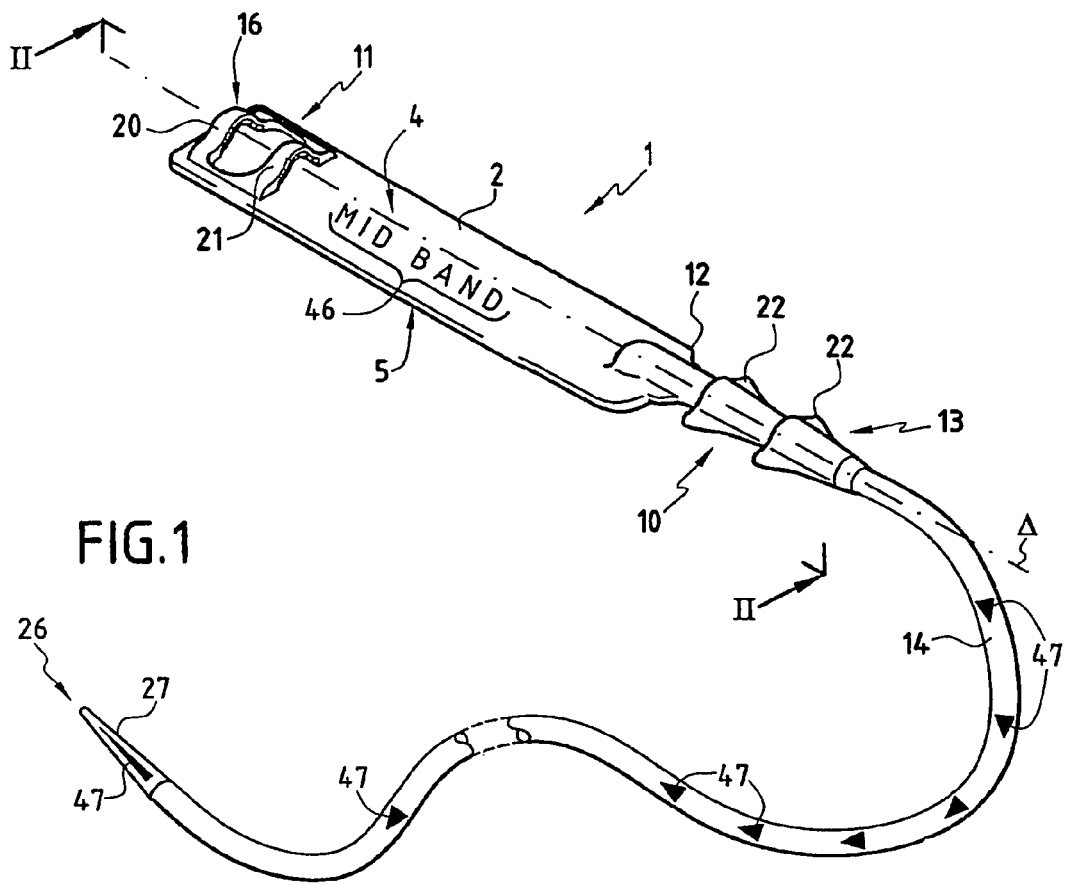
FIG. 1 is a perspective in a state of rest of a gastric belt according to the invention.

A gastric belt according to the invention, illustrated in FIGS. 1 to 3 and designated in its entirety by reference numeral 1, comprises a tubular body 2 which defines at least one tight inflatable chamber 3. According to the example illustrated, the body 2 has, in plan view elevation, a general rectangular shape, which corresponds to a preferred embodiment, without nevertheless constituting the sole form which can be adopted for the body 2.

In a deflated state of the chamber 3, it must also be considered that the body 2 has a general flat form and a transverse cross-section, such as more particularly illustrated in FIG. 3, substantially rectangular, the inflatable chamber 3 having a transverse cross-section of general form likewise forming a rectangle.

The gastric belt 1 thus has a back 4 and a work face 5, for coming into contact with the zone of the oesophagus or stomach, at the level of which the belt shall be placed, as will emerge hereinbelow.

Figure 4:
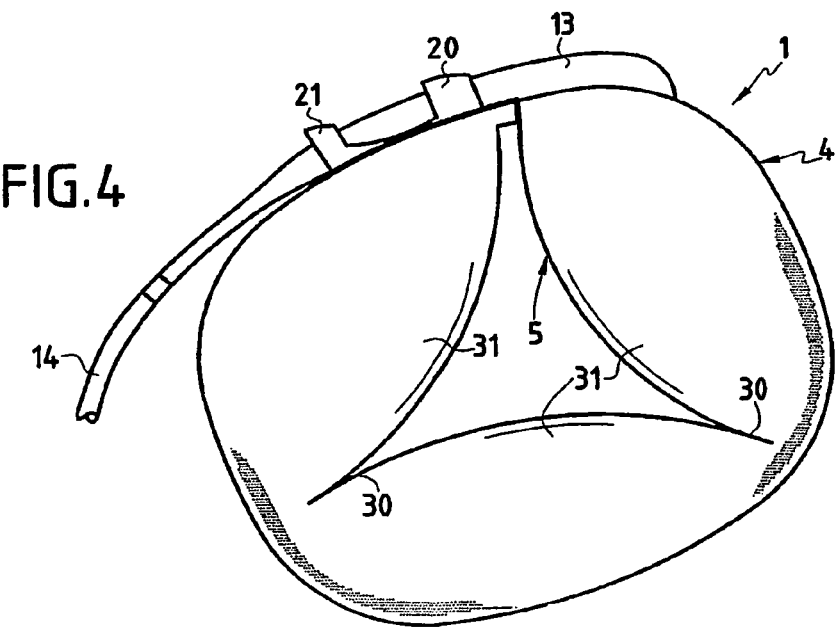
FIG. 4 is a view of the inflatable gastric belt according to FIG. 1 in a state of a closed and semi-inflated ring.

So as to allow the belt 1 to close into a ring, as shown in FIG. 4, the belt 1 also comprises connecting means 10 and 11 equipping the two ends of the belt. The connecting means 10 and 11 can be made by any appropriate means.

According to the example illustrated, the connecting means 10 first comprise, at a first so-called inflation end 12 of the body 2, a tail 13 connecting a catheter 14 to the inflatable chamber 3.

According to the example illustrated, the connecting tail 13 thus extends substantially in the longitudinal extension of the body 2 and has an internal duct 15 connected to the chamber 3. Of course, this duct 15 communicates with the internal conduit of the catheter 14.

The connecting means 11, situated at the end opposite the inflation end 12 and free end 16, are, according to the example illustrated, constituted by at least one and, in the present case, two bows 20, 21 arranged at the back 4 of the body 2 and intended to receive the tail 13.

According to the example illustrated, the two bows 20 are situated at a distance from one another and the tail 13 comprises blocking or anti-return means 22 for preventing any untimely withdrawal of the connecting tail 13 after engagement of the latter in the bows 20, 21. According to the example illustrated, the anti-return blocking means comprise two configurations 22 as a spruce tree or lanceolated, which are each supposed to cooperate with a corresponding bow 20, 21.

According to the example illustrated, the bow 20, situated closest to the free end 16 of the body 2, has a width $l_{20}$ measured parallel to the longitudinal axis $\Delta$ of the body 2 and, at the apex of the bow 20, greater than 5 mm. This arrangement of the invention thus allows the first bow to ensure guiding of the catheter 14 during the procedure of closing the belt. According to the example illustrated, the width $l_{2o}$ of the first bow is greater than the width $l_{21}$ of the second bow.

Also, still according to the example illustrated, in order to promote passage of the catheter and as far as possible reduce efforts necessary for this surgical procedure, the bows have, on their internal face, a row of stria 25 which reduce the contact surface of the catheter with the corresponding bow, so as to reduce frictional forces. The stria 25 extend parallel to the longitudinal axis $\Delta$ of the body 2 and in the direction of introduction of the catheter 14. So as to further reduce the force necessary for passage of the catheter 14, it can likewise be envisaged to cover the outer surface of the catheter 14 with a coating having a low friction coefficient, such as, for example, Teflon.

Figure 5:
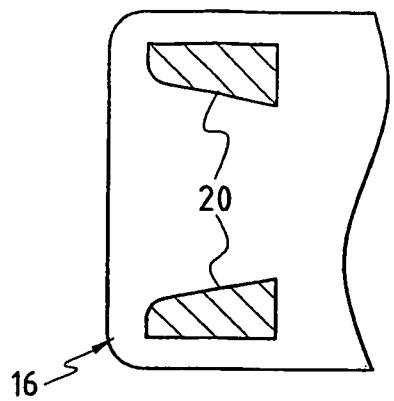
FIG. 5 is a partial section, according to the line V-V of FIG. 2.

Still in terms of greater ease of introduction of the catheter 14, the first bow 20 preferably has a form flared towards the free end of the body 2 and converging towards the second ring 21, as illustrated in FIG. 5.

Similarly, the free end 26 of the catheter 14 is blocked by a plug 27, conical in shape, which prevents materials from entering the duct of the catheter and facilitates introduction of the catheter into the bow 20 during closing of the belt.

The plug 27 shall be sectionalised after closing of the belt, for placing the inflation means, not shown.

The inflatable gastric belt 1 can be made out of any biocompatible material adapted, such as for example, from biocompatible silicon or of implantable grade, which confers on the body 2 the suppleness and the elasticity necessary for inflation of the chamber 3.

The connecting means 10, 11 are thus used to close the inflatable belt 1 into a ring, as illustrated in FIG. 4.

According to the invention, the body 2 is realised such that, during inflation of the chamber 3, folds 30 form, conferring on the section of passage defined by the belt 1 in a ring shape an irregular star shape or again a likewise irregular hypocycloidal shape, as shown more particularly in FIG. 2. Each fold 30 corresponds to a zone where the work face 5 is folded down or folded back locally on itself, such that the regions of the work face 5 adjacent to the fold 30 and situated on either side of the fold 30 are in contact.

To attain this desired objective of irregular or random form for the section of passage defined by the gastric belt 1 closed into a ring and inflated, the body 2 is realised such that the length $l_5$ of the wall of the inflatable chamber 3, forming the work face 5, has a length greater than or equal to the length $l_4$ of the wall of the inflatable chamber 3 forming the back 4 of the belt 1, when said belt is in the deflated state.

According to the example illustrated, the length of the wall 5 of the inflatable chamber 3 is substantially equal to that of the wall of the same chamber 3 making up the back 4 of the belt of the gastric belt 1.

According to the embodiment illustrated, so as to avoid problems of deflation of the different pockets 31 formed by the folds 30, the internal wall of the inflatable chamber 3, making up the back 4, has two rows of fluting or grooves of longitudinal directions 35 which extend, preferably though not necessarily, over the entire length of the internal wall of the inflatable chamber 3. These grooves 35 are thus for forming channels at the folds for passage of the inflation fluid from the chamber 3. According to the example illustrated, the two rows of grooves 35 are placed at a distance from one another and each near a longitudinal edge 36 of the body 2.

It should be emphasised that the folds 30 made by the inflatable belt 1 according to the invention contribute to ensuring good stability of the latter at the level of the wall of the oesophagus or stomach and delimit the rolling movements likely to induce inflammation of said stomach or oesophagus wall.

According to the invention, to further increase this stability, it is likewise provided to utilise local limitation means 37 of the elasticity of the wall of the inflatable chamber 3 making up the work face 5. According to the example illustrated, these limitation means 37 of the local elasticity are constituted by a longitudinal median zone of the wall 5 which has excessive thickness 37 relative to two lateral belts 38 of this same wall 5. Accordingly, during inflation of the chamber 3, dilation of the wall 5 intervenes preferably on the edges 38 of the belt and the median region of the wall 5 thus has a radius of curvature greater than that of the lateral edges or lateral zones 38, as shown in FIG. 6. This advantageous characteristic of the invention thus contributes to the stability of the belt by reducing the rocking tendency of the latter.

Furthermore, according to another characteristic of the invention, to guarantee better control of the stomach restriction formed by the belt 1, it is likewise provided to incorporate in the wall of the body 2 making up the back 4 a supple inextensible fitting 40. Accordingly, during inflation of the chamber 3, the belt 1 recognises essentially centripetal deformation. The supple fitting 40 can be made from any supple adapted inextensible material, such as, for example though not exclusively, Dacron material.

The fitting 40 is preferably completely embedded in the wall of the body 2 forming the back 4 and is completely enclosed by the material constituting the body 2.

Also, according to the example illustrated, it should be noted that the longitudinal internal edges 41 of the inflatable chamber 3 are situated at a distance $d_{4l}$ greater than 0.5 mm and, preferably, between 0.50 mm and 2.50 mm from the corresponding longitudinal edge 36 of the body 2, with a distance of between 0.65 mm and 0.90 mm offering a good compromise. This characteristic also contributes to stability of the belt 1 around the wall of the oesophagus or stomach.

According to another characteristic of the invention, the end 45 of the chamber 3, situated to the side of the free end 16 of the body 2, is likewise at a distance from said end and, preferably, at a distance $d_{45}$ greater than 5 mm and, particularly preferred, between 7 mm and 15 mm and equal, according to the example, to 10 mm at least, so as to define a full zone at which it is possible to take the belt via forceps, without the risk of perforating the wall of the inflation chamber 3. To further reinforce resistance to perforation of the end of the belt, the wall of the inflatable chamber has excessive thickness at its end oriented towards the free end 16 of the body 2.

This characteristic of the invention contributes to facilitating the placing of the gastric belt by means of coelioscopic surgical tools.

Furthermore, according to the example illustrated, to prevent deviation of the two ends 12 and 16 of the body 2, when the belt 1 is closed into a ring, the bow 20, situated closest to the free end 16, is placed at a distance $d_{2o}$ from the corresponding end 16 of the body 2 less than or equal to 5 mm and, preferably, less than 3 mm.

According to the invention, to make the work of the surgeon easier using the coelioscope, optical position-finding means 46 can be used for the back or dorsal face 4 and/or the work face 5 of the body 2. According to the example illustrated in FIG. 1, these position-finding means 46 comprise identification characters of the belt placed on the back 4, while the work face is blank. Accordingly, observation of these indications via endoscope informs the surgeon of the orientation of the body of the belt. According to the example illustrated, the indications 46 are completed by a row of marks 47, arranged on the face of the corresponding catheter 14 of the back 4 of the body 2. The marks 47 each have the form of a triangle of which an apex is facing the end and oriented towards the free end 26 of the catheter, such that they likewise fulfil a function of optic indication means of the direction of the free end of the catheter. Being able to see the marks 47 thus makes it easier for the surgeon to place the belt.

According to the embodiment described earlier in relation to FIG. 2, the free reinforced end 16 of the body of the belt is constituted by a full zone. All the same, in terms of the invention, the reinforced end is not necessarily made in this way. Accordingly, FIGS. 7 and 8 illustrate another embodiment of this reinforced end.

Figure 8:
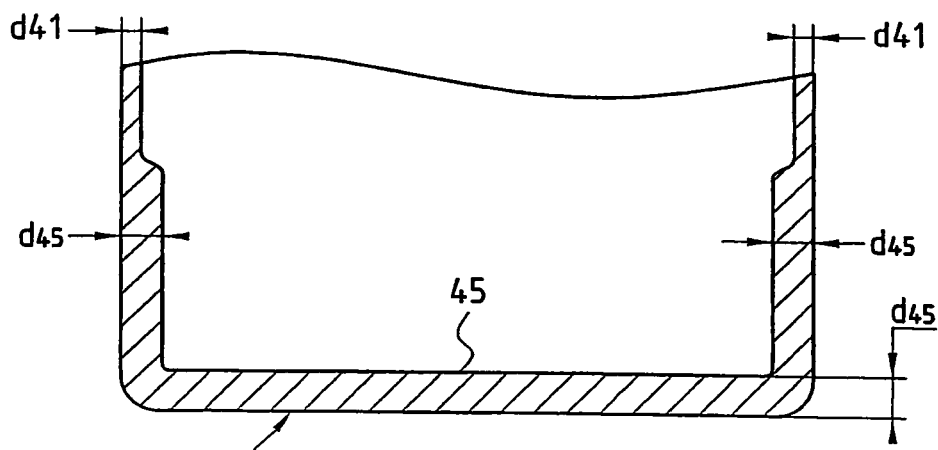
FIG. 8 is a partial section according to the line VIII-VIII of FIG. 7.

According to this other embodiment, the distance $d_{45}$, separating the inner edge of the inflatable chamber 3 from the corresponding external edge of the body 2, is augmented locally in the end region of the body relative to the distance $d_{4l}$ separating the internal edge of the chamber 3 from the edge corresponding of the body 2 for the rest of the belt, as shown in FIG. 8. According to the example illustrated, the distance $d_{45}$ is selected to be between 1.50 mm and 2.50 mm. This local augmentation on three sides reduces the risks of deterioration of the belt by a prehension clip at the free end.

Figure 7:
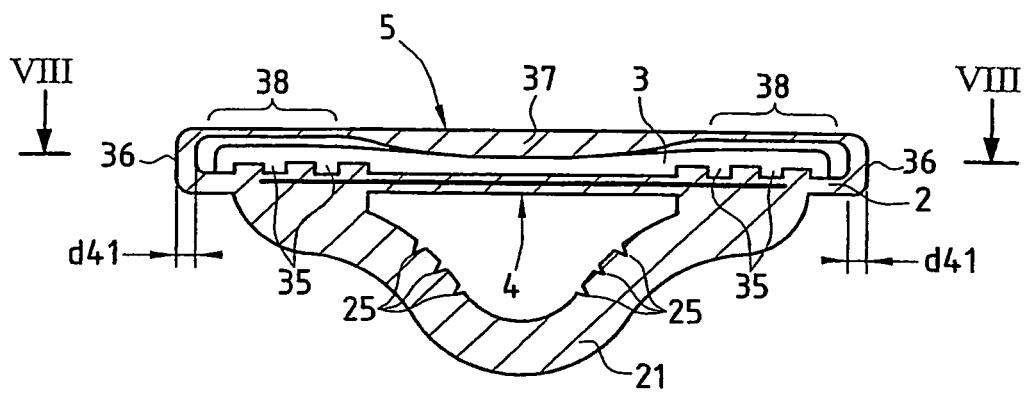
FIG. 7 is a section, similar to FIG. 3, showing a variant embodiment of a reinforced end of the belt.

In addition, according to the example illustrated, this arrangement is completed by local augmentation of thickness of the wall making up the work face 5, near the end 16 of the body 2, as shown in FIG. 7.

Of course, various other modifications can be made to the invention without departing from its scope.

The invention claimed is:
1. An inflatable gastric belt comprising:
    an elongated tubular body (2) with an inflation end (12) and a free end (16), made of supple material which is, in part at least, elastically deformable, which defines a tight inflatable chamber (3) with ends and which can be in a deflatable state and a back (4) formed by a wall of the chamber (3) and a work face (5) which is formed by another wall of the chamber (3),
    connecting means (10,11) arranged relative to the two ends (12, 16) of the tubular body (2) and allowing the belt to close in the form of a ring, the work face (5) being arranged inside the ring,
an inflation catheter (14) with a free end (26) and tightly connected to the inflatable chamber and intended to be connected to the inflation means, wherein the wall of the chamber (3) forming the work face (5), has, in the deflated state of the belt, a length ($l_5$) greater than or equal to the length ($l_4$) of the wall of the chamber (3) forming the back (4), such that, during closing of the belt and after inflation, the wall of the chamber, constituting the work face (5), forms folds (30) such that a section of passage as a result of closing of the belt into the ring is hypocycloidal-shaped and wherein each fold comprises a fold in the work face (5) with regions of the work face on either side of the fold in contact with each other.
2. The inflatable gastric belt as claimed in claim 1, wherein any point of a wall of the chamber (3) has, on an internal face thereof at least one groove (35) of longitudinal direction, for defining an internal duct for circulation of an inflation fluid at the folds (30).

3. The inflatable gastric belt as claimed in claim 2, wherein the internal face of a wall of the chamber (3) comprises at least one row of parallel longitudinal grooves (35).

4. The inflatable gastric belt as claimed in claim 2, wherein the at least one groove is arranged on the internal face of a wall of the chamber (3) forming the back (4) of the belt.

5. The inflatable gastric belt as claimed in claim 1, wherein an internal face of a wall of the chamber (3) forming the back (4) of the belt comprises two rows of parallel longitudinal grooves (35), each row being situated near an edge (36) of the back (4) of the belt.

6. The inflatable gastric belt as claimed in claim 1, wherein the wall of the chamber (3), forming the work face (5), comprises means for locally limiting the elasticity (37) of the wall (5).

7. The inflatable gastric belt as claimed in claim 6, wherein the work face has longitudinal edges and in that the locally limiting means of the elasticity (37) occupy a median longitudinal region of the work face, such that, during inflation of the belt, the longitudinal edges of the work face dilate more than the median region of said work face.

8. The inflatable gastric belt as claimed in claim 6, wherein the local limitation means of the elasticity (37) comprise a local extra thickness of the wall of the chamber (3) making up the work face of the belt (5).

9. The inflatable gastric belt as claimed in claim 1, wherein the inflatable chamber (3) has longitudinal edges (44) and in that each longitudinal edge (44) of the inflatable chamber (3) is situated at a distance from a corresponding longitudinal edge (36) of the body (2) of the belt.

10. The inflatable gastric belt as claimed in claim 1, wherein the inflatable chamber (3) has longitudinal edges (44) and in that each longitudinal edge (44) of the inflatable chamber (3) is situated at a distance ($d_{4l}$) from a corresponding longitudinal edge of the body (2) of the belt, between 0.50 mm and 2 mm.

11. The inflatable gastric belt as claimed in claim 1, wherein the wall of the inflatable chamber (3), forming the back (4) of the belt, comprises at least one longitudinal inextensible and supple fitting (40), such as to promote centripetal deformation of the chamber (3), when the belt is closed during inflation.

12. The inflatable gastric belt as claimed in claim 11, wherein the body (2) is injection-moulded around the inextensible fitting (40) and forms a one-piece unit which completely encloses said inextensible fitting (40).

13. The inflatable gastric belt as claimed in claim 1, wherein the connecting means (10, 11) comprise:

in relation to the inflation end (12) of the body (2), a connecting tail (13) of the catheter (14) on the inflatable chamber (3), and, in relation to the free end (16) of the body (2), at least one bow (20) for receiving the connecting tail (13).

14. The inflatable gastric belt as claimed in claim 13, wherein the connecting tail (13) comprises at least anti-return locking means (22) for cooperating with the bow (20).

15. The inflatable gastric belt as claimed in claim 14, wherein the anti-return locking means comprise at least a configuration (22) as a spruce tree or arrow.

16. The inflatable gastric belt as claimed in claim 13, wherein the bow (20) is arranged at the back of the belt.

17. The inflatable gastric belt as claimed in claim 13, wherein the connecting means (11) comprise at least two aligned bows, a first bow (20), and a second bow (21), the first bow (20) being situated closest to the free end (16) of the body (2) having a width ($l_{20}$), measured parallel to the longitudinal axis of the body, greater than a width ($l_{21}$) of the second bow (21), so as to define a tunnel for guiding the catheter (14) towards the second bow.

18. The gastric belt as claimed in claim 13, wherein the bow (20) has a width measured parallel to the longitudinal axis of the body greater than 5 mm.

19. The gastric belt as claimed in claim 13, wherein the bow (20,21) has an internal face, which has striae (25) parallel to the longitudinal axis ($\Delta$) of the body (2), so as to reduce friction as the catheter passes.

20. The gastric belt as claimed in claim 1, wherein the catheter (14) is covered in a product with low friction coefficient.

21. The gastric belt as claimed in claim 1, wherein at least one end (45) of the inflatable chamber (3) is situated at a distance from the free end (16) of the body (2) to define a reinforced grip end.

22. The gastric belt as claimed in claim 21, wherein the distance ($d_{45}$) between at least one end (45) of the inflatable chamber (3) and the free end (16) of the body (2) is greater than or equal to 1.50 mm at the reinforced grip end.

23. The gastric belt as claimed in claim 13, wherein the at least one bow (20), in relation near the free end (16) of the body (2), is placed at a distance ($d_{20}$) of less than 5 mm.

24. The gastric belt as claimed in claim 1, comprising position-finding means (46) of the back (4) and/or of the work face (5) of the body (2).

25. The gastric belt as claimed in claim 1, comprising indication means (47) which indicates a direction of one or both of the free end (26) of the catheter (14) and the free end (16) of the body (2).

26. The gastric belt as claimed in claim 23, wherein the distance ($d_{20}$) is less than 3 mm.

* * * * *

UNITED STATES PATENT AND TRADEMARK OFFICE
CERTIFICATE OF CORRECTION

PATENT NO.        : 8,657,735 B2
APPLICATION NO. : 10/586344
DATED             : February 25, 2014
INVENTOR(S)       : Frering et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1726 days.

Signed and Sealed this

Twenty-ninth Day of September, 2015

Michelle K. Lee
*Director of the United States Patent and Trademark Office*